United States Patent [19]

Webb et al.

[11] Patent Number: 4,996,061
[45] Date of Patent: Feb. 26, 1991

[54] PHARMACEUTICAL COMPOSITION FOR PIPERIDINOALKANOL-DECONGESTANT COMBINATION

[75] Inventors: Norval E. Webb, Middletown; Gregory V. Hammer, West Chester, both of Ohio

[73] Assignee: Merrell Dow Pharmaceuticals Inc., Cincinnati, Ohio

[21] Appl. No.: 438,966

[22] Filed: Dec. 28, 1989

Related U.S. Application Data

[63] Continuation-in-part of Ser. No. 379,728, Jul. 14, 1989, abandoned, which is a continuation of Ser. No. 211,308, Jun. 24, 1988, abandoned, Continuation-in-part of Ser. No. 105,939, Oct. 7, 1987.

[51] Int. Cl.$^5$ .............................................. A61K 9/36
[52] U.S. Cl. .................................. 424/475; 424/479; 424/480; 514/929
[58] Field of Search ...................... 424/471, 479, 480; 514/929

[56] References Cited

U.S. PATENT DOCUMENTS

| | | | |
|---|---|---|---|
| 4,126,502 | 11/1978 | Dabal | 156/184 |
| 4,361,545 | 11/1982 | Powell et al. | 424/19 |
| 4,540,566 | 9/1988 | Dacrs et al. | 514/964 |
| 4,795,327 | 1/1989 | Gaylord et al. | |

FOREIGN PATENT DOCUMENTS 111144 10/1983 European Pat. Off. .

OTHER PUBLICATIONS

W. C. Gunsel, Compression-Coated and Layered Tablets, Chapter 4, Pharmaceutical Dosage Forms: Tablets, Lieberman, H. A. and Lackman, L., editors, New York and Basil, Marcel Dekker, Inc., vol. 1 (1980).

*Primary Examiner*—Olik Chaudhuri
*Assistant Examiner*—Andrew Griffis
*Attorney, Agent, or Firm*—Louis J. Wille

[57] ABSTRACT

The present invention relates to a pharmaceutical composition in the form of a multiple-compression tablet comprising (a) a discrete zone made with Formulation (A) which comprises a carrier base material combined with a therapeutically effective decongestant amount of a sympathomimetic drug, or a pharmaceutically acceptable salt thereof, the carrier base material being a mixture of (i) one or more pharmaceutically acceptable water-soluble nonionic cellulose ethers in an amount from about 18% to about 50% by weight of Formulation (A), (ii) one or more pharmaceutically acceptable anionic surfactants in an amount from about 2% to about 20% by weight of Formulation (A), and (iii) one or more other pharmaceutically acceptable excipients, and (b) a discrete zone made with Formulation (B) which comprises a second carrier base material combined with a therapeutically effective antihistaminic amount of a piperidinoalkanol, or a pharmaceutically acceptable salt thereof, the second carrier base being a mixture of (i) calcium carbonate in an amount from about 0.5% to about 25% by weight of Formulation (B), (ii) one or more pharmaceutically acceptable nonionic surfactants in an amount from about 1% to about 10% by weight of Formulation (B), and (iii) one or more other pharmaceutically acceptable excipients, wherein Formulation (B) optionally also contains a therapeutically effective decongestant amount of a sympathomimetic drug, or a pharmaceutically acceptable salt thereof;

with the proviso that when said pharmaceutical composition is in the form of a compression-coated tablet, the inner core zone is made with Formulation (A) and the outer coat zone is made with Formulation (B).

12 Claims, No Drawings

PHARMACEUTICAL COMPOSITION FOR PIPERIDINOALKANOL-DECONGESTANT COMBINATION

CROSS-REFERENCE TO RELATED APPLICATION

This is a continuation-in-part of application Ser. No. 379,728, filed July 14, 1989, which is a continuation of application Ser. No. 211,308, filed June 24, 1988, which is a continuation-in-part of application Ser. No. 105,939, filed Oct. 7, 1987, all now abandoned.

Various piperidinoalkanol derivatives are disclosed in U.S. Pat. Nos. 3,878,217, 4,254,129 and 4,285,957 as compounds useful as antihistamines, antiallergy agents, and bronchodilators. Included within the scope of these generically defined piperidinoalkanols is α-[4-(1,1-dimethylethyl)phenyl]-4-(hydroxydiphenylmethyl)-1-piperidinebutanol which is commercially available as a pharmaceutical composition in solid unit dosage form for the treatment of patients with symptoms of seasonal allergic rhinitis. These antihistamines are generally effective when administered orally in unit dosage form on a twice a day dosage schedule wherein the unit dosage form provides immediate-release of the active medicament. For example, the recommended dosage for α-[4-(1,1-dimethylethyl)phenyl]-4-(hydroxydiphenylmethyl)-1-piperidinebutanol in humans is 60 mg. b.i.d.

Various sympathomimetic drugs such as pseudoephedrine, phenylephrine and phenylpropanolamine, are recognized by those skilled in the art as therapeutic agents effective in the relief of nasal congestion and are commonly administered concomitantly with antihistamines for relief of nasal congestion associated with allergic rhinitis. These sympathomimetic drugs are generally effective when administered orally in unit dosage form on a four times a day dosage schedule wherein the unit dosage form provides immediate-release of the active medicament. For example, the recommended dosage for pseudoephedrine hydrochloride in adults is 60 mg every 6 hr (q.i.d.). In addition, unit dosage forms containing sympathomimetic drugs can be formulated to provide prolonged release of the active medicament so as to allow the effective daily dose to be administered on a less frequent dosage schedule. For example, the recommended dosage for pseudoephedrine hydrochloride in a prolonged-release formulation can be 120 mg. b.i.d.

Accordingly, the present invention relates to a pharmaceutical composition in the form of a multiple-compression tablet comprising a discrete zone made from a formulation which provides sustained-release of a therapeutically effective decongestant amount of a sympathomimetic drug and a discrete zone made from a different formulation which provides immediate release of a therapeutically effective antihistaminic amount of a piperidinoalkanol and, optionally, a therapeutically effective decongestant amount of a sympathomimetic drug.

More specifically, the present invention provides a pharmaceutical composition in the form of a multiple-compression tablet comprising (a) a discrete zone made from Formulation (A) which comprises a carrier base material combined with a therapeutically effective decongestant amount of a sympathomimetic drug, or a pharmaceutically acceptable salt thereof, the carrier base material being a mixture of (i) one or more pharmaceutically acceptable water-soluble nonionic cellulose ethers in an amount from about 18% to about 50% by weight of Formulation (A), (ii) one or more pharmaceutically acceptable anionic surfactants in an amount from about 2% to about 20% by weight of Formulation (A), and (iii) one or more other pharmaceutically acceptable excipients, and (b) a discrete zone made from Formulation (B) which comprises a second carrier base material combined with a therapeutically effective antihistaminic amount of a piperidinoalkanol, or a pharmaceutically acceptable salt thereof, the second carrier base being a mixture of (i) calcium carbonate in an amount from about 0.5% to about 25% by weight of Formulation (B), (ii) one or more pharmaceutically acceptable nonionic surfactants in an amount from about 1% to about 10% by weight of Formulation (B), and (iii) one or more other pharmaceutically acceptable excipients, wherein Formulation (B) optionally also contains a therapeutically effective decongestant amount of a sympathomimetic drug, or a pharmaceutically acceptable salt thereof;

As used herein, the term "sympathomimetic drug" refers to those sympathomimetic agents which are therapeutically effective in providing relief of nasal congestion in a patient suffering therefrom including, but not limited to, pseudoephedrine, phenylephrine, and phenylpropanolamine. As is well recognized and appreciated by those skilled in the art, these sympathomimetic drugs can be used according to the present invention as free amines or as pharmaceutically acceptable salts thereof. The term "pharmaceutically acceptable salts" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. The preferred acid addition salts are those prepared from hydrochloric acid, sulfuric acid or tartaric acid. Any of the above salts are prepared by conventional methods well known in the art.

A therapeutically effective decongestant amount of a sympathomimetic drug is that amount which produces the desired decongestant therapeutic response upon oral administration and can be readily determined by one skilled in the art by the use of conventional techniques and by observing results obtained under analogous circumstances. In determining the therapeutically effective amount, a number of factors are considered, including but not limited to: the particular compound administered; the bioavailability characteristics of the pharmaceutical composition administered; the dose regimen selected; and other relevant circumstances.

A therapeutically effective decongestant amount of a sympathomimetic drug will vary from about 1 mg to about 200 mg. Preferred amounts will vary from about 5 mg to about 150 mg.

It is understood that a therapeutically effective decongestant amount of a sympathomimetic drug is present in Formulation (A) and, optionally, in Formulation (B) of the pharmaceutical composition of the present invention. The carrier base material of Formulation (A) provides a prolonged or sustained release of the active medicament whereas the carrier base material of Formulation (B) provides an immediate release of the active medicament(s). As used herein, the term "sustained-release" refers to a property of the pharmaceutical composition wherein the absorption and bioavailability of the active medicament is maintained in a time-release pattern such that therapeutically effective decongestant amounts of the sympathomimetic drug are bioavailable over an extended period of time. The term "immediate-release" refers to a property of the pharmaceutical composition wherein the entire dose of active medicament is made bioavailable without substantial delay.

Where therapeutically effective decongestant amounts of a sympathomimetic drug are present in both Formulation (A) and Formulation (B) of the unit dosage form of the present invention, it is preferred that from about 50% to about 95% of the total dose of the sympathomimetic drug is present in Formulation (A). It is most preferred that from about 80% to about 95% of the total dose is present in Formulation (A).

In a particularly preferred embodiment of the present invention, with respect to the sympathomimetic drug, about 110 mg of pseudoephedrine hydrochloride is in Formulation (A) and about 10 mg of pseudoephedrine hydrochloride is in Formulation (B).

It is, of course, understood by the present invention that the sympathomimetic drug in Formulation (A) can be different from that in Formulation (B). However, it is preferred that the sympathomimetic drug in Formulation (A) and in Formulation (B) are the same.

Piperidinoalkanol derivatives which are useful as antihistamines are disclosed in U.S. Pat. Nos. 3,878,217, 4,254,129 and 4,285,957 and these patents are incorporated herein by reference. For purposes of the present invention the preferred piperidinoalkanol is $\mu$-[(1,1-dimethylethyl)phenyl]-4-(hydroxydiphenylmethyl)-1-piperidinebutanol. These piperidinoalkanols can be used according to the present invention as the free compound or as a pharmaceutically acceptable salt thereof as described in the above patents.

A therapeutically effective antihistaminic amount of a piperidinoalkanol is that amount which produces the desired antihistaminic therapeutic response upon oral administration and can readily be determined by one skilled in the art as described above for the sympathomimetic drugs. The amount will vary from about 0.1 mg to about 140 mg. The preferred therapeutically effective antihistaminic amount will vary from about 20 mg to about 70 mg with about 60 mg being most preferred.

It is understood that a therapeutically effective antihistaminic amount of a piperidinoalkanol is present in Formulation (B) of the pharmaceutical composition of the present invention. This Formulation (B) provides for immediate release of the active medicament.

In a particularly preferred embodiment of the present invention with respect to the piperidinoalkanol, about 60 mg of $\alpha$-[4-(1,1-dimethylethyl)phenyl]-4-(hydroxydiphenylmethyl)-1-piperidinebutanol is present in Formulation (B).

The pharmaceutically acceptable water soluble nonionic cellulose ethers which are effective in the present invention include, but are not limited to, commercially available, high viscosity grades of methylcellulose, including 1,500 and 4,000 cps viscosity grades of Methocel A and Metalose SM, as well as high viscosity grades of hydroxypropylmethylcellulose, including the 4,000 cps viscosity grades of Methocel E and Metalose 60SH, the 4,000 cps viscosity grades of Methocel F and Metalose 65SH the 5,000, 12,000, 20,000, and 75,000 cps viscosity grades of Methocel J and the 4,000, 15,000 and 100,000 cps viscosity grades of Methocel K and the 4,000, 15,000 and 39,000 cps viscosity grades of Metalose 90SH. Methocel K4M (2208) is preferred.

The amount of nonionic cellulose ether in Formulation (A) of the pharmaceutical composition of the present invention can vary from about 18% to about 50% by weight of Formulation (A). Compositions wherein the nonionic cellulose ether makes up from about 24% to about 36% are preferred.

The pharmaceutically acceptable anionic surfactants which are effective in the present invention include alkali metal sulfates of linear and branched alcohols, ethoxylated alcohols, ethoxylated alkylphenols, ethoxylated acids, ethoxylated amides, oils, fatty esters, etc., alkali metal salts of sulfonates of naphthalene, alkylnaphthalenes, naphthalene condensates, alkyl-substituted benzenes, diphenyl derivatives, $\alpha$-olefins, petroleum, oils, fatty acids, etc., as well as the alkali metal salts of dialkyl sulfosuccinates.

Representative anionic surfactants include sodium or potassium dodecyl sulfate, sodium octadecyl sulfate, sodium sulfated castor oil, sodium dodecylbenzene sulfonate, sodium linear alkylate sulfonate, sodium sulfonated mineral oil, sodium petroleum sulfonate, sodium salt of naphthalene-sulfonic acid-formaldehyde condensate, dioctyl sodium sulfosuccinate the the like. Sodium dodecyl sulfate is preferred.

The amount of anionic surfactant in Formulation (A) of the pharmaceutical composition of the present invention can vary from about 2% to about 20% by weight of the Formulation (A) composition. Compositions wherein the anionic surfactant makes up from about 5% to about 15% are preferred.

The pharmaceutical acceptable nonionic surfactants which are effective in the present invention includes pharmaceutically acceptable nonionic surfactants known in the art of pharmaceutical science, such as, for example, Polysorbate 80 (also known as Tween 80), and various poloxamers or pluronics, or mixtures thereof. The preferred nonionic surfactant in the pharmaceutical composition of the present invention is Polysorbate 80.

The amount of the nonionic surfactant in Formula (B) of the pharmaceutical composition of the present invention can vary from about 1% to 10% by weight of Formulation (B). Compositions wherein the nonionic surfactant makes up from about 2% to about 6% are preferred.

The amount of calcium carbonate present in Formulation (B) of the pharmaceutical composition of the present invention can vary from about 0.5% to about 25% by weight of the Formulation (B). Compositions wherein the calcium carbonate makes up from about 5% to about 20% are preferred, with compositions wherein the calcium carbonate makes up about 15% being most preferred.

Formulation (A) and Formulation (B) of the pharmaceutical compositions of the present invention also contain one or more other pharmaceutically acceptable excipients. These excipients are therapeutically inert ingredients such as are well known and appreciated in the art. Such excipients include, for example, conventional carriers (such as lactose, corn starch or derivatives thereof, talc, stearic acid or salts thereof, methyl cellulose or derivatives thereof including hydroxypropylmethylcellulose, and the like), preserving agents, stabilizing agents, disintegrants, sweetening agents, coloring agents, flavoring agents, antioxidants, buffers, and the like. Selection of a particular ingredient or ingredients and the amounts used can be readily determined by one skilled in the art by reference to standard procedures and practices.

Preferred compositions of the present invention are those wherein pregelatinized corn starch (Starch 1500), microcrystalline cellulose (Avicel), starch glycolate sodium (Explotab), and magnesium stearate are present as other pharmaceutically acceptable excipients in Formulation (B).

Preferred amounts of the above excipients are from about 25% to about 45%, 20% to 40%, 1% to 10%, and 0.1% to 1%, respectively, by weight of Formulation (B) with about 35%, 30%, 5%, and 0.55%, respectively, being most preferred.

Preferred compositions of the present invention are those wherein colloidal silicon dioxide and zinc stearate are present as other pharmaceutically acceptable excipients in Formulation (A). Preferred amounts of the above excipients are from about 0.1% to about 5% and from about 0.5% to about 10%, respectively, by weight of Formulation (A) with about 0.5% and 1.5%, respectively, being most preferred.

The ingredients of the pharmaceutical composition according to the present invention are brought together into a form of a multiple-compression tablet for oral administration according to standard practice and procedures well known in the art of pharmaceutical science using conventional formulation and manufacturing techniques.

The multiple-compression tablet of the present invention is a compression tablet which is formed by two or more compression cycles. Each compression cycle uses, alternatively, granulations made from either Formulation (A) or Formulation (B). This results in a multiple-compression tablet which has at least two discrete zones defined by the presence of either Formulation (A) or Formulation (B) in the zone. The multiple-compression tablets of the present invention have at least two discrete zones, one defined by the presence of Formulation (A) and one defined by the presence of Formulation (B). A multiple-compression tablet of the present invention can exist as a layered tablet, as a compression-coated tablet, or as an inlay tablet.

A layered tablet is a tablet which is made up of two or more distinct layers or discrete zones of granulation compressed together with the individual layers lying one on top of another. Layered tablets have the appearance of a sandwich because the edges of each layer or zone is exposed. Such conventional layered tablets are generally prepared by compressing a granulation onto a previously compressed granulation. The operation may be repeated to produce multilayered tablets of more than two layers. A layered tablet of the present invention has at least two layers or discrete zones one of which is made from Formulation (A) and another of which is made from Formulation (B).

A compression-coated tablet is a tablet which is made up of an inner core and and one or more outer coats wherein the inner core is completely surrounded by the outer coat or coats. These tablets have at least two discrete zones of granulation compressed together, i.e., an inner core zone and an outer coat zone. Such tablets, also referred to as press-coat or dry-coated tablets, are prepared by feeding a previously compressed inner core into a special tableting machine and compressing one or more other granulation coats around the preformed inner core. A compression-coated tablet of the present invention has an inner core or inner core zone made from Formulation (A) and at least one press-coat or press-coat zone made from Formulation (B).

A variation of the compression-coated tablet is the inlay tablet, also referred to as a dot, or bull's-eye tablet. Instead of an inner core zone being completely surrounded by an outer coat, one surface of the zone corresponding to an inner core zone is exposed. These tablets have at least two discrete zones of granulation compressed together, i.e., an inlay zone and a base zone. The preparation of inlay tablets is similar to the preparation of compression-coated tablets except that a surface of coating is eliminated. An inlay tablet of the present invention has at least two discrete zones, one of which is made from Formulation (A) and another of which is made from Formulation (B).

In a preferred embodiment of the present invention, the multiple-compression tablet is in the form of a compression-coated tablet. Compression-coated tablets of the present invention can generally be manufactured by a three-step procedure involving preparation of the inner core and outer coat granulations from Formulation (A) and Formulation (B), respectively, compressing the inner core granulation to provide the inner core tablet, and subsequently compressing an outer coat granulation around the inner core tablet so as to provide two discrete zones with the inner core zone defined by Formulation (A) and the outer coat zone defined by Formulation (B).

It is of course understood that the multiple-compression tablets produced according to the present invention can be film coated using standard ingredients and procedures commonly used and well known in the art of pharmaceutical science. It is contemplated that tablets so coated are within the scope of the present invention.

In a preferred embodiment of the present invention tablets are formulated and manufactured using the procedure as described in Example 1. This example is not intended to limit the scope of the invention in any way.

EXAMPLE 1

Preparation of Tablets Containinq
α-[4-(1,1-Dimethylethyl)phenyl]-4-(hydroxydiphenylmethyl)-1-piperidinebutanol and Pseudoephedrine Hydrochloride Step A: Formulation (A)

Combine 110 g pseudoephedrine hydrochloride (milled if necessary), 108 g of hydroxypropylmethylcellulose (2208), 15 g of sodium dodecyl sulfate, (sodium lauryl sulfate), 1.5 g of sodium dioxide, 61 g of lactose and mix thoroughly using a high-intensity type mixture such as the Collette Gral. Pass 1.5 g of zinc stearate through a 30-mesh screen, add to the above mixture and continue mixing.

Form compacted tablets (slugs) using a tablet press. Mill the slugs and separate the granulation into coarse and fine granules by using a screening device. The fine powder mix may be compacted first to facilitate slugging. Reslug, mill and screen the coarse granules as necessary, to obtain a suitable granulation.

Pass 3.0 g of zinc stearate through a 30-mesh screen, add to the fine granules above, and blend in a mixer such as a V-blender.

Step B: Formulation (B)

Combine 60 g of α-[4-(1,1-dimethylethyl)phenyl]-4-(hydroxydiphenylmethyl)-1-piperidinebutanol 85.7 g of microcrystalline cellulose, 125 g of pregelatinized corn starch, and 87.5 g of calcium carbonate and mix thoroughly. Prepare a granulating solution by dissolving 17.5 g of Polysorbate 80 in about 177.3 g of purified water and add to the above mixture. Mix until well formed granules are produced. Wet screen the granulation if necessary.

Dry the granulation to a moisture level of not more than 3% (O'Haus moisture measuring device). Screen the dried granulation into coarse and fine granules and mill the coarse granules using size reduction equipment such as a Fitzmill. Combine the milled coarse granules and the fine granules and mix in a mixer. To this granulation, add 191.3 g of a mixture of 10 g of pseudoephedrine hydrochloride, 87.5 g of microcrystalline cellulose, 62.5 g of pregelatinized corn starch and 31.3 g of starch glycolate sodium and mix thoroughly. Add 3.0 g of magnesium stearate (screened) and continue mixing until a suitable mixture is obtained.

Step C: Tablet Compression a. Press-coat tablet: Feed the inner core granulation [Formulation (A)]into a tablet press and form inner core tablet with an average weight of 290-310 mg, a hardness of 1-7 kp (Schleuninger), and a thickness of 4.5-5.5 mm.

Feed the inner core tablet into a tablet press charged with the outer coat granulation [Formulation (B)]and compress the outer coat around the inner core tablet to provide the finished compression-coated tablet. About 1000 tablets are made with an average weight of 835-905 mg, a hardness of 5-15 kp (Schleuninger) and friability of NMT 1%.

b. Layered tablet: Feed the granulations prepared from Formulation (A) and Formulation (B) into a tablet press suitable for preparing conventional multilayer tablets. Prepare a layered tablet with one layer made from Formulation (A) and another layer made from Formulation (B). The layer made from Formulation (A) is made with an average weight of 290-310 mg. About 1000 tablets are made with an average weight of 835-905 mg.

We claim:

1. A pharmaceutical composition in the form of a multiple-compression tablet comprising
   (a) a discrete zone made with Formulation (A) which comprises a carrier base material combined with a therapeutically effective decongestant amount of a sympathomimetic drug, or a pharmaceutically acceptable salt thereof, the carrier base material begin a mixture of (I) one or more pharmaceutically acceptable water-soluble nonionic cellulose ethers in an amount from about 18% to about 50% by weight of Formulation (A), (ii) one or more pharmaceutically acceptable anionic surfactants in an amount from about 2% to about 20% by weight of Formaulation (A), and (iii) one or more other pharmaceutically acceptable excipients, wherein said carrier base material provides a sustained release of the sympathomimetic drug, and
   (b) a discrete zone made with Formulation (B) which comprises a second carrier base material combined with a therapeutically effective antihistaminic amount of a piperidinoalkanol, or a pharmaceutically acceptable salt thereof, the second carrier base being a mixture of (i) calcium carbonate in an amount from about 0.5% to about 25% by weight of Formulation (B), (ii) one or more pharmaceutically acceptable nonionic surfactants in an amount from about 1% to about 10% by weight of Formulation (B), and (iii) one or more other pharmaceutically acceptable excipients, wherein Formulation (B) optionally also contains a therapeutically effective decongestant amount of a sympathomimetic drug, or a pharmaceutically acceptable salt thereof, and wherein said second carrier base material provides an immediate release of the piperidinoalkanol and of any sympathomimetic drug.

2. A composition of claim 1 in the form of a compression-coated tablet.

3. A composition of claim 2 wherein the sympathomimetic drug is pseudoephedrine.

4. A composition of claim 2 wherein the piperidinoalkanol is $\alpha$-[4-(1,1-dimethylethyl)phenyl]-4-(hydroxydiphenylmethyl)-1-piperidinebutanol.

5. A composition of claim 2 wherein the sympathomimetic drug is pseudoephedrine and the piperidinoalkanol is $\alpha$[4-(1,1-dimethylethyl)phenyl]-4-(hydroxydiphenylmethyl)-1-piperidinebutanol.

6. A composition of claim 5 wherein the inner core zone contains from about 100 mg to about 120 mg of pseudoephedrine hydrochloride and outer coat zone contains from about 20 mg to about 70 mg of $\alpha$-[4-(1,1-dimethylethyl)phenyl]-4-(hydroxydiphenylmethyl)-1-piperidinebutanol and from about 0 mg to about 20 mg of pseudoephedrine hydrochloride.

7. A composition of claim 6 wherein the inner core zone carrier base material contains from about 5% to about 15% sodium dodecyl sulfate as the anionic surfactant.

8. A composition of claim 6 wherein the outer coat zone carrier base material contains from about 2% to about 6% of Polysorbate 80 as the nonionic surfactant and from about 5% to about 20% of calcium carbonate.

9. A composition of claim 8 wherein the outer coat zone carrier base material contains about 15% of calcium carbonate.

10. A composition of claim 7 wherein the outer coat zone carrier base material contains from about 2% to about 6% of Polysorbate 80 as the nonionic surfactant and from about 5% to about 20% of calcium carbonate.

11. A composition of claim 10 wherein the outer coat zone carrier base material contains about 15% of calcium carbonate.

12. The pharmaceutical composition of claim 1 wherein the tablet is compression coated, the inner core is made with formulation (A) and the outer zone is made with Formulation (B).

* * * * *

UNITED STATES PATENT AND TRADEMARK OFFICE
CERTIFICATE OF CORRECTION

PATENT NO. : 4,996,061
DATED : February 26, 1991
INVENTOR(S) : Norval E. Webb and Gregory V. Hammer It is certified that error appears in the above-identified patent and that said Letters Patent is hereby corrected as shown below:

Column 3, Line 31 patent reads: "µ" and should read --α--

Column 6, Line 51 patent reads: "sodium dioxide" and should read --silicon dioxide--

Claim 1, Column 7, Line 49 patent reads: "begin a mixture of (I)" and should read --being a mixture of (i)--

Claim 1, Column 7, Line 56 patent reads: "Formaulation" and should read --Formulation--

Signed and Sealed this

Twenty-eighth Day of July, 1992

Attest:

DOUGLAS B. COMER

*Attesting Officer*  *Acting Commissioner of Patents and Trademarks*